(12) United States Patent
Bell-Booth

(10) Patent No.: US 11,159,874 B2
(45) Date of Patent: Oct. 26, 2021

(54) WEARABLE DEVICE

(71) Applicant: EARSHOTS LIMITED, Palmerston North (NZ)

(72) Inventor: James Bell-Booth, Palmerston North (NZ)

(73) Assignee: EARSHOTS LIMITED, Palmerston North (NZ)

(\*) Notice: Subject to any disclaimer, the term of this patent is extended or adjusted under 35 U.S.C. 154(b) by 0 days.

(21) Appl. No.: 16/494,490

(22) PCT Filed: Mar. 19, 2018

(86) PCT No.: PCT/NZ2018/050034
§ 371 (c)(1),
(2) Date: Sep. 16, 2019

(87) PCT Pub. No.: WO2018/174728
PCT Pub. Date: Sep. 27, 2018

(65) Prior Publication Data
US 2020/0092626 A1 Mar. 19, 2020

(30) Foreign Application Priority Data
Mar. 20, 2017 (NZ) .................................. 730305

(51) Int. Cl.
*H04R 1/10* (2006.01)
*A61B 5/00* (2006.01)
(Continued)

(52) U.S. Cl.
CPC ........... *H04R 1/105* (2013.01); *A61B 5/0022* (2013.01); *A61B 5/02055* (2013.01);
(Continued)

(58) Field of Classification Search
CPC .................. H04R 1/105; H04R 1/1008; H04R 1/1016; H04R 1/1041; H04R 2420/07;
(Continued)

(56) References Cited

U.S. PATENT DOCUMENTS

| 4,827,524 A | 5/1989 | Rising |
| 8,098,865 B2 | 1/2012 | Ho et al. |

(Continued)

FOREIGN PATENT DOCUMENTS

| CN | 205320237 U | 6/2016 |
| CN | 106488355 A | 3/2017 |

OTHER PUBLICATIONS

First Examination Report received in Chinese Patent Application No. 2018800199168 dated Dec. 16, 2020.
Extended European Search Report received in European Patent Application No. 18770230.3 dated Dec. 4, 2020.
(Continued)

*Primary Examiner* — William A Jerez Lora
(74) *Attorney, Agent, or Firm* — Burns & Levinson, LLP; Joseph M. Maraia

(57) ABSTRACT

A wearable device for attachment to the ear of a user that includes a magnetic attachment system. The wearable device includes an earpiece including a speaker and a body section including a hook for attachment about the ear. First and second magnetic elements are provided on the earpiece and body. The earpiece is movable relative to the body section and the earpiece and body section are configured so that when the body section is hooked about the ear the magnetic elements are magnetically attracted to each other through the ear to retain the device in place.

19 Claims, 12 Drawing Sheets

(51) Int. Cl.
  *A61B 5/0205* (2006.01)
  *A61B 5/11* (2006.01)
(52) U.S. Cl.
  CPC ............ *A61B 5/1112* (2013.01); *A61B 5/683* (2013.01); *A61B 5/6815* (2013.01); *H04R 1/1016* (2013.01); *H04R 1/1041* (2013.01); *A61B 2562/0219* (2013.01); *H04R 2420/07* (2013.01)
(58) Field of Classification Search
  CPC .............. A61B 5/0022; A61B 5/02055; A61B 5/1112; A61B 5/6815; A61B 5/683; A61B 2562/0219
  USPC ........................... 381/23.1, 74, 312, 330, 381
  See application file for complete search history.

(56) References Cited

U.S. PATENT DOCUMENTS

| | | | |
|---|---|---|---|
| 10,856,068 B2* | 12/2020 | Qian | H04R 1/1041 |
| 2005/0025329 A1* | 2/2005 | Lee | H04R 1/105 |
| | | | 381/370 |
| 2014/0251023 A1* | 9/2014 | Magomedov | A61B 5/11 |
| | | | 73/779 |
| 2015/0195639 A1* | 7/2015 | Azmi | H04R 1/1033 |
| | | | 381/74 |
| 2015/0208183 A1 | 7/2015 | Bern | |
| 2016/0381448 A1* | 12/2016 | Qian | H04R 1/105 |
| | | | 381/74 |

* cited by examiner

US 11,159,874 B2

WEARABLE DEVICE

CROSS REFERENCE TO RELATED APPLICATIONS

This application is a United States national phase application under 35 U.S.C. 371 of co-pending International Patent Application Number PCT/NZ2018/050034, filed on Mar. 19, 2018, which claims priority to New Zealand Patent Application No. 730305, filed on Mar. 20, 2017, disclosures of which are incorporated herein by reference in their entireties for all purposes.

FIELD

This invention relates to a wearable device for attachment to the ear of a user that includes a magnetic attachment system that is particularly, although not exclusively, suited for use during active use, such as during physical work or sporting activities.

BACKGROUND

There are currently a number of different designs for earphones and headphones on the market aiming to provide a secure and comfortable fit for the majority of users. These are generally designed for passive listening rather than for use during active sporting activities. Earphones, due to their more compact and lightweight nature are commonly used for exercise where there may be a wide range of dynamic movements. In such an active environment, a generic earbud design is likely to fall out as there is no specific anchoring to the ear and they often require wires to the media device for audio input, which may catch during movement and cause the earbuds to fall out.

Many earphones have multiple sizes of silicone or foam sleeves to provide a more personalised fit. However without specific anchoring to the ear, these have similar problems to a generic design. Proposed anchoring systems include a fixed or flexible loop that hooks around the back of the ear, securing the earphone, and a hook inside the ear. Although these both come in a range of sizes and styles, they generally require the ear to conform to a specific shape and can be uncomfortable for some users for whom the shape is not suited. The hook around the ear design also requires the earbud to be deep in the ear canal which may cause damage. Custom moulded solutions also exist, however these can be expensive and unsuitable as a mass produced item for the general market.

Magnetic attachment mechanisms have been incorporated into earphones but are not suitable for use during active use for a range of reasons. They do not provide sufficient anchoring to retain an earphone during energetic and varied movements. Many do not fit to a wide range of ear shapes and do not have any means of adjustment allowing fit to be optimized for a user. In some cases, the positions of the magnets may actually move the center of mass of the earphones away from the ear and promote dislodging of the device from the ear under energetic movement.

It is an object of the invention to provide a wearable device for secure attachment to the ear of a user or to at least provide the public with a useful choice.

SUMMARY

According to one example embodiment there is provided a wearable device for attachment to an ear including:
i. an earpiece including a speaker and a first magnetic element; and
ii. a body section including a hook for attachment about the ear and a second magnetic element, wherein the earpiece is movable relative to the body section and the earpiece and body section are configured so that when the body section is hooked about the ear the first magnetic element and second magnetic element are adapted to be magnetically attracted to each other through the ear to retain the device in place.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e., they will be taken to mean an inclusion of the listed components which the use directly references, and possibly also of other non-specified components or elements.

Reference to any document in this specification does not constitute an admission that it is prior art, validly combinable with other documents or that it forms part of the common general knowledge.

BRIEF DESCRIPTION OF THE DRAWINGS

The accompanying drawings which are incorporated in and constitute part of the specification, illustrate embodiments of the invention and, together with the general description of the invention given above, and the detailed description of embodiments given below, serve to explain the principles of the invention, in which.

DETAILED DESCRIPTION

Figure 1:
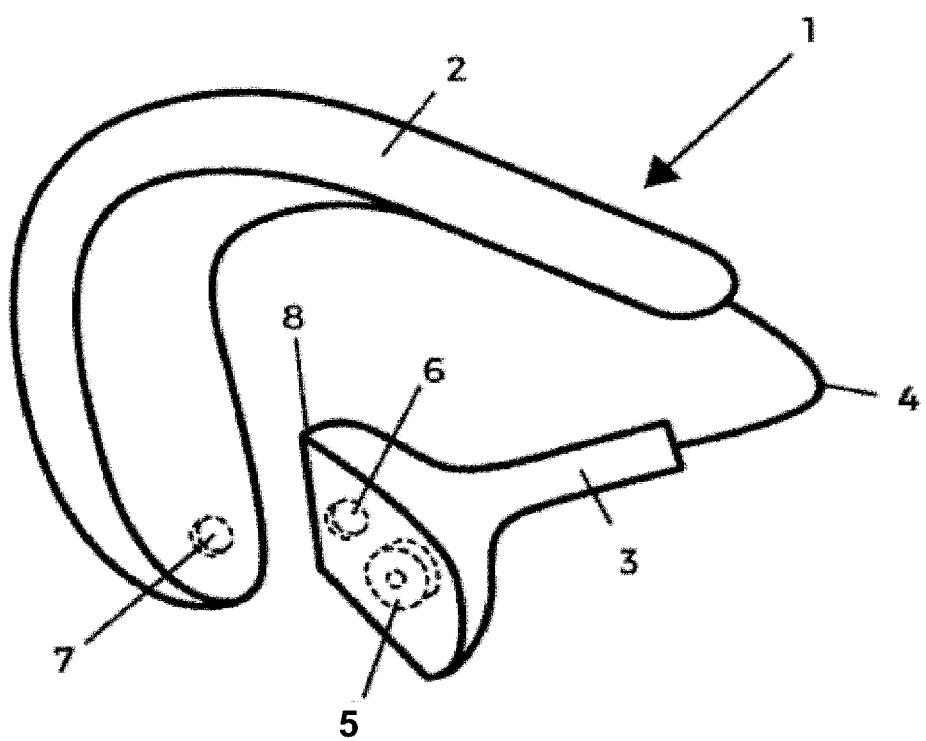
FIG. 1 shows a perspective view of a wearable device according to one embodiment.
Figure 2:
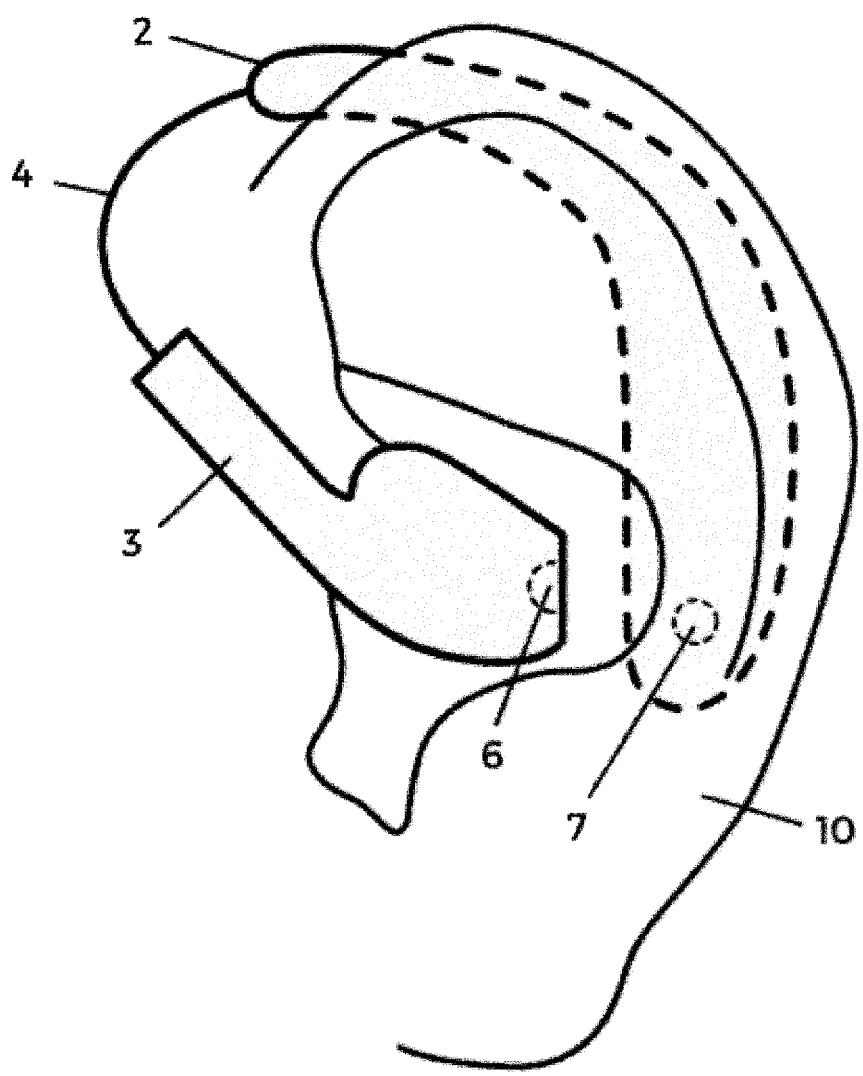
FIG. 2 shows the wearable device of FIG. 1 when worn on the ear of a user.

Disclosed below are wearable devices for attachment to an ear that may be a simple earphone or which may include a media player and/or wireless communication circuit and/or a microprocessor and/or bio sensors or other sensors. For a simple wired earphone a wire may provide a signal to drive an earphone in the device. For a wireless embodiment the device will require a battery and a circuit for receiving wireless signals and driving the earphone. The circuit may include a microprocessor to receive information from sensors and to modify the operation of the device based on sensed information and wireless information received.

FIGS. 1 to 5 show a wearable device 1 including a body section 2 in the form of a "hook" configured to engage around the upper part of the region connecting the ear to the skull of a user. The hook may be dimensioned to surround a circle having a radius of between 20 to 32 mm, preferably 25 mm to 27 mm. The body section may have a length of between 10 mm and 100 mm and a thickness of between 0.1 mm and 20 mm. The body section 2 may be flexible to wrap around the ear of a user and may be twisted so as to direct the weight of the body section into the skull of a user. A coating may be provided on internal faces for user comfort (otherwise the attractive force between the magnets may impose an uncomfortable force on a user's ear) formed of a thermoplastic elastomer or silicone (siloxane) of hardness range between Shore A 30 to Shore A 90, preferably about Shore A 40. Due to the strong attractive forces of the magnets the silicon may not be able to retain the magnets and the magnets may need to be physically retained by a rigid element of the body or bonded to the body.

In this embodiment an earpiece 3 is connected to the body section via a flexible connection, in this case a cable 4 which provides an electrical signal from the body section to drive speaker 5. Earpiece 3 may suitably have a length of between 13 mm and 22 mm and a width of between 10 mm and 16 mm. The cable 4 may suitably have a length of between 10 mm and 60 mm and a width of between 0.1 mm and 8 mm.

Figure 3:
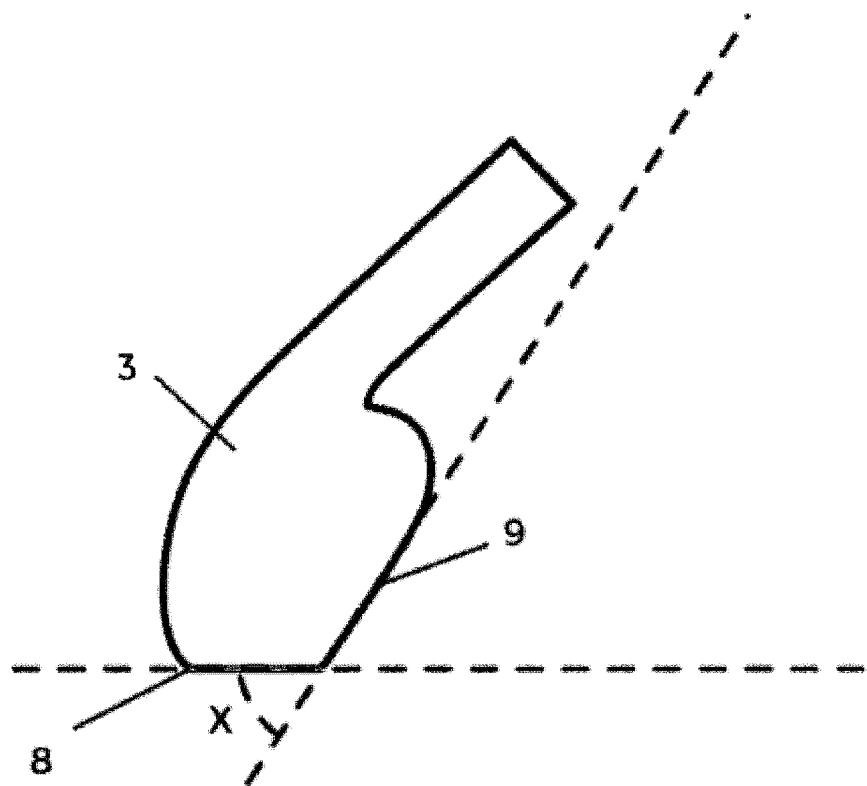
FIG. 3 shows the geometry of the earphone of the wearable device shown in FIG. 1.

As shown in FIG. 3 a distal face 8 of earpiece 3 is disposed at an angle x with respect to the face 9 of the earpiece which opposes the ear canal. The angle x is preferably within the range of 30° and 60° and preferably between 50° and 55°. This angle is important to correctly dispose the earpiece with respect to the ear canal but also to apply the correct forces to the earpiece and body section so as to urge them tightly against the ear of a user so as to be secured during vigorous exercise.

The body section 2 includes a magnetic element 7 and the earpiece includes a magnetic element 6. It will be appreciated that one of magnetic elements 6 and 7 may be a magnet and the other may simply be a magnetic material, such as a ferromagnetic steel, or both may be magnets. Small, strong neodymium magnets are preferred. In the following description both elements will simply be referred to as magnets but it will be appreciated that any elements providing suitable magnetic attraction between them may be utilized. That being said high strength permanent magnets do produce strong magnetic attraction for small component size.

In the embodiment of FIGS. 1 to 5 a single magnet 6 is provided on the earpiece 3 and a single magnet 7 is provided on the body 2. Magnet 6 may be a permanent magnet having a volume of between 6 mm$^3$ and 440 mm$^3$, preferably between 150 mm$^3$ and 175 mm$^3$, having a magnetic field strength of between 368 gauss and 1200 gauss. Magnet 7 is preferably a permanent magnet having a volume of between 2 mm$^3$ and 63,000 mm$^3$, preferably between 400 mm$^3$ and 440 mm$^3$, having a magnetic field strength of between 4500 gauss and 8000 gauss (typically producing a pull of between 3 to 5 pounds). The magnets may suitably be in the form of a cylinder, rectangular block, hexagonal tube, multiple individual magnetic beads or semicylinder etc.

In this embodiment the dimensions of body section 2 and length of flexible cable 4 and positions of the magnets will be optimized for a range of standard ear shapes.

Figure 4:
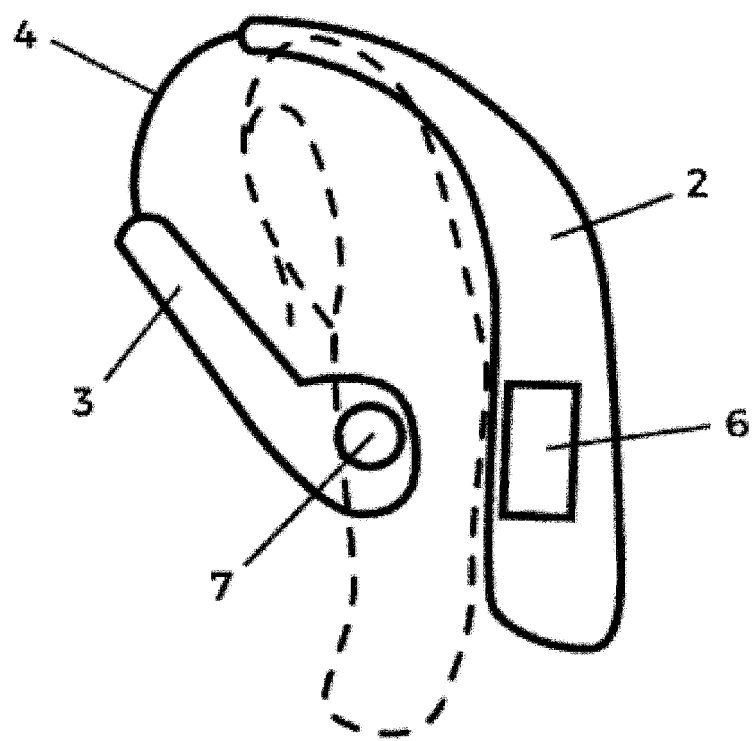
FIG. 4 shows a view along the major plane of the ear with the wearable device of FIG. 1 positioned on the ear of a user.
Figure 5:
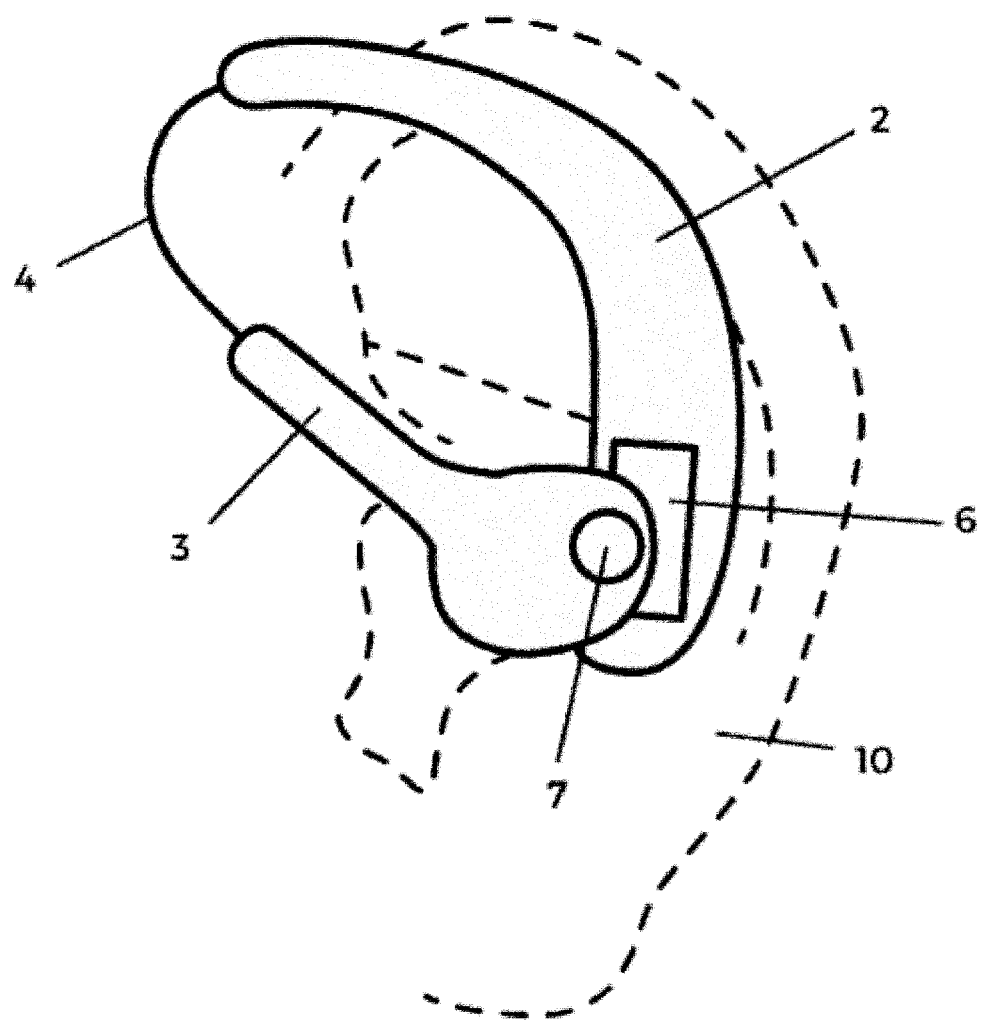
FIG. 5 shows a side view of the ear, normal to the view shown in FIG. 4, with the wearable device of FIG. 1 positioned on the ear of a user.

In use the body section 4 is hooked over about the ear of a user as shown in FIGS. 4 and 5 and the earpiece 3 is brought into alignment with the body section 2 so that magnets 6 and 7 are strongly attracted to one another and hold the body section 2 and earpiece 3 tightly against a user's ear. The magnets are positioned and the earpiece 3 and body section 2 configured so that the magnets are proximate the concha of a user's ear when in use. Attachment in this region securely attaches the device to a user's ear and forces the earpiece and body section towards the ear to secure them in place. Further, the end of the body section 2 proximate cable 4 may be flexible so that as the magnets attract the distal end of the body section may wrap around the ear of a user to tightly conform to the shape of the ear. Alternatively or additionally cable 4 may be formed of a stretchable material to enhance this effect.

Figure 6:
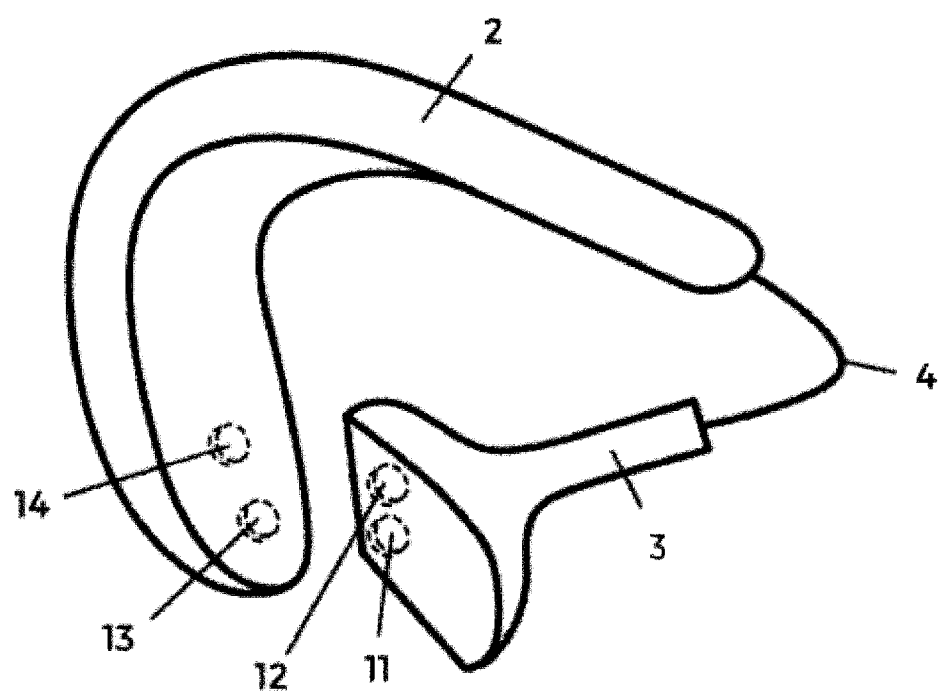
FIG. 6 shows a perspective view of a wearable device according to another embodiment.

Referring now to FIG. 6 a modified embodiment for controlling earpiece and body section alignment is shown (like components being given like numerals). In this embodiment a pair of magnets 11 and 12 are provided on earpiece 3 and a corresponding pair of magnets are provided on body section 2. Magnets 12 and 14 attract each other and magnets 11 and 13 also attract each other. This arrangement prevents rotation of the earpiece relative to body section 2 to provide more precise alignment.

Figure 7:
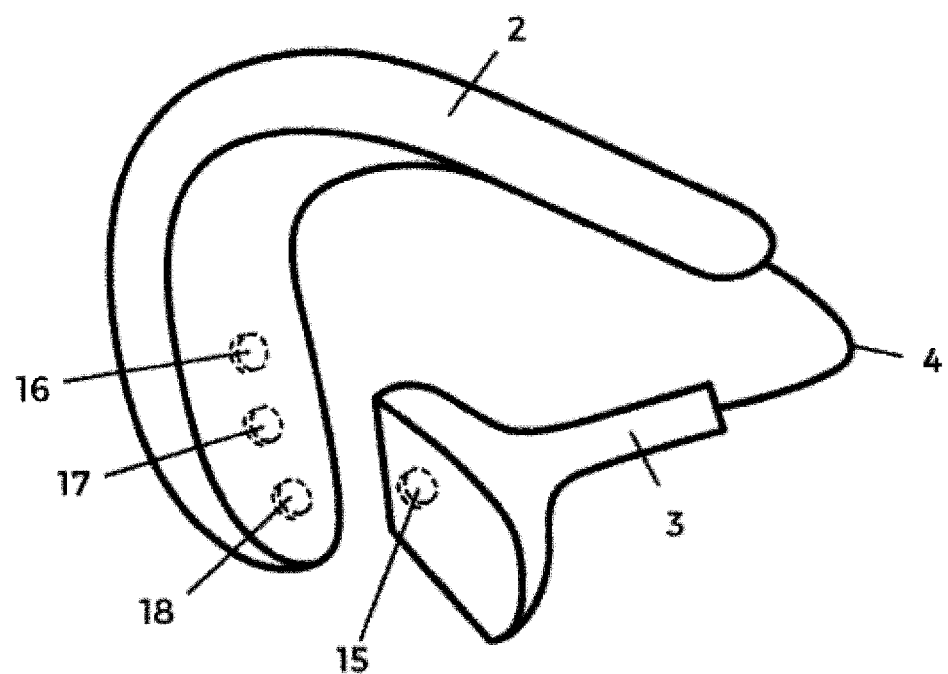
FIG. 7 shows a perspective view of a wearable device according to a further embodiment.

Referring now to FIG. 7 a further modified embodiment is shown (like components being given like numerals). In this case one magnet 15 is provided on earpiece 3 and a series of magnets are provided on body section 2. This allows a user to align magnet 15 with any one of magnets 16 to 18 in the position providing the best fit. This allows one design to fit tightly for a range of ears sizes. It will be appreciated that more than one magnet may be provided on earpiece 3. For example, if two magnets are provided they may align with either magnets 16 and 17 or 17 and 18. This provided both the adjustability of this embodiment and the anti-rotation aspect of the previous embodiment.

Figure 8:
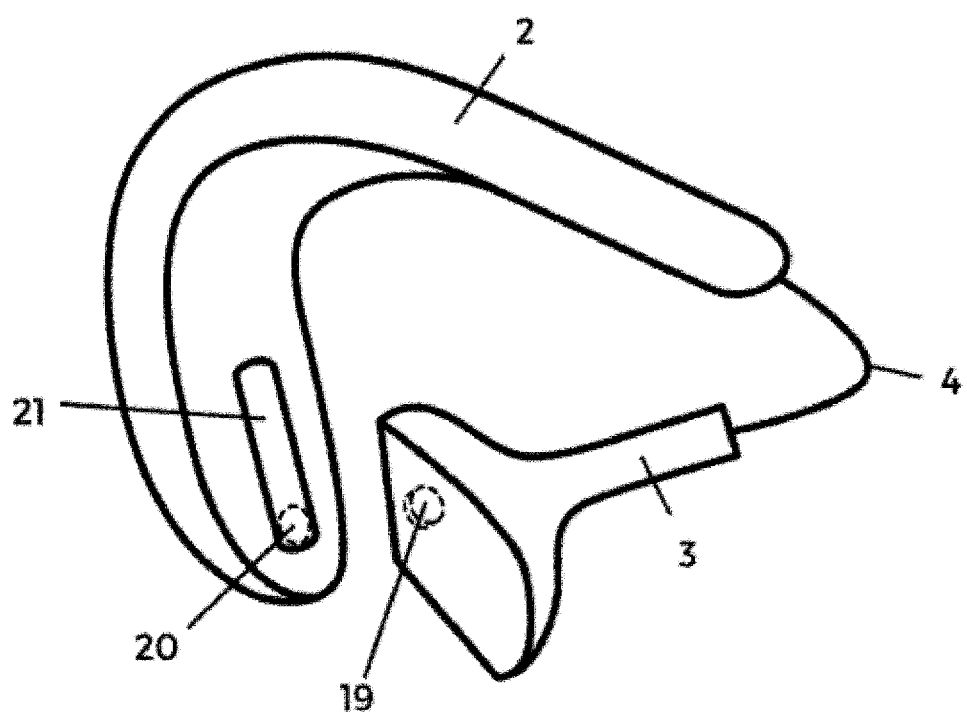
FIG. 8 shows a perspective view of a wearable device according to a further embodiment.

FIG. 8 shows a further embodiment in which a single magnet 19 is provided on earpiece 3 and a single magnet 20 is provided in a track 21 on body section 2. The magnet 20 may slide along track 20 to be positioned in the optimum position for a user's ear.

Figure 9:
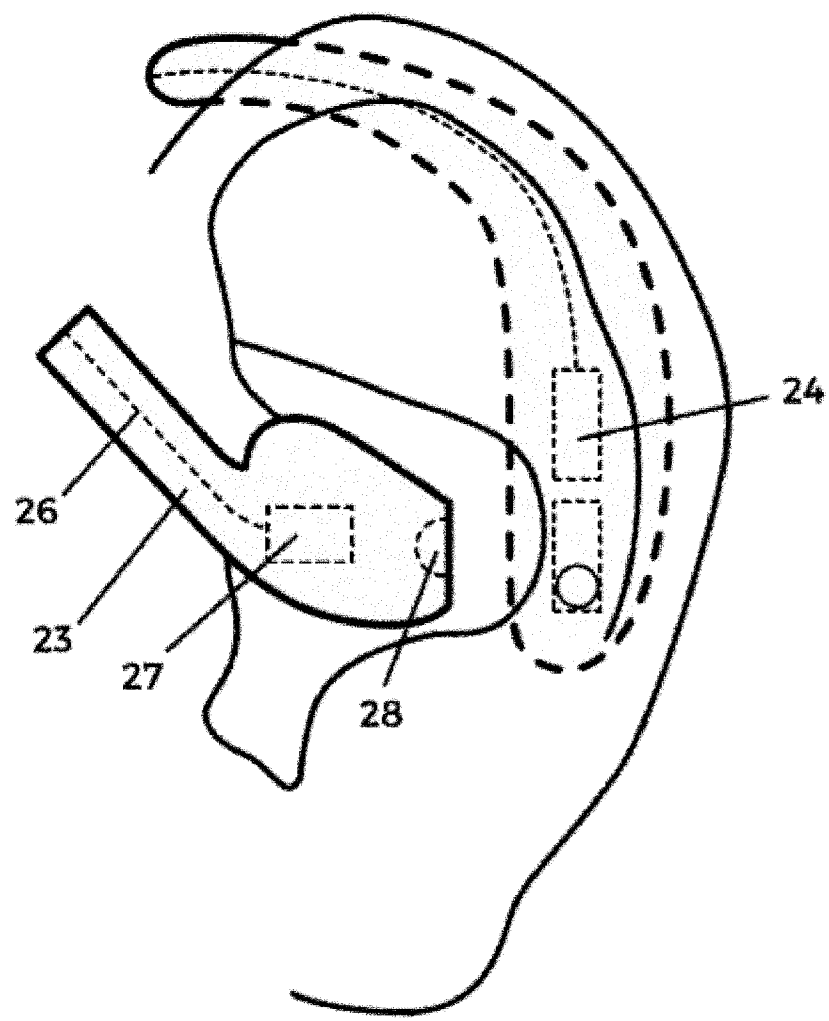
FIG. 9 shows a perspective view of a wireless wearable device according to a further embodiment.
Figure 10:
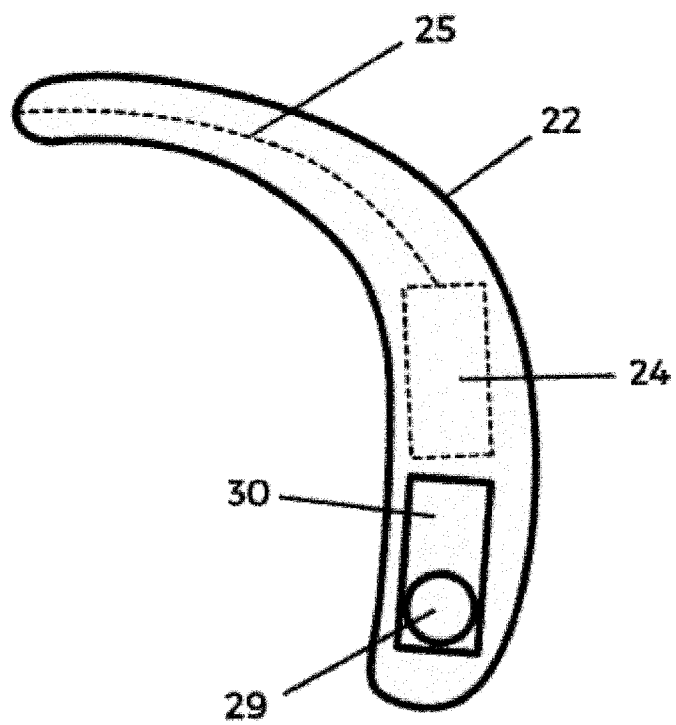
FIG. 10 shows the body section of the wearable device shown in FIG. 9.

Referring now to FIGS. 9 and 10 a wireless embodiment is shown including a body section 22 and an earpiece 23 having similar form to those shown in the previous embodiments. However, in this embodiment circuit 24 of body section 22 communicates wirelessly via antenna 25 to antenna 26 and circuit 27 of earpiece 27. In this embodiment a single magnet 28 is provided on earpiece 23 and a single magnet 29 is provided in a track 30, similar to the embodiment of FIG. 8. It will be appreciated that the other embodiments may be adopted in a wireless solution too.

Figure 11A:
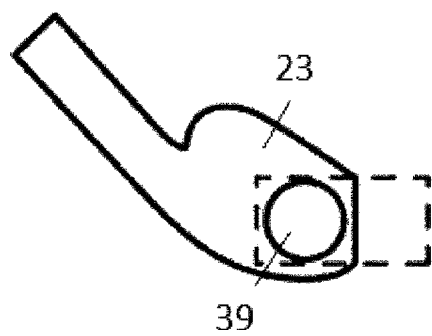
FIGS. 11a and 11b show an earphone with an extendable magnet.
Figure 11B:
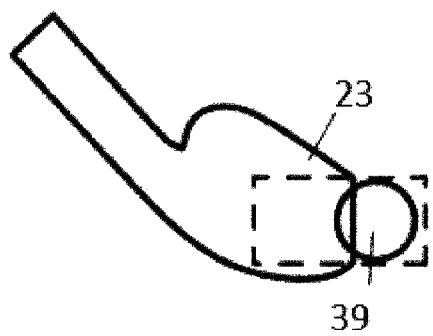

FIGS. 11a and 11b show a modified earpiece design in which a magnet 39 may be positioned in a first retracted position with respect to earpiece 23 as shown in FIG. 11a and a second extended position in which magnet 39 may be positioned in an extended position with respect to earpiece 23 as shown in FIG. 11b. In this manner the positioning of magnet 39 with respect to earpiece 23 may be continuously adjusted to optimally position the earpiece 23 with respect to a user's ear.

Figure 12:
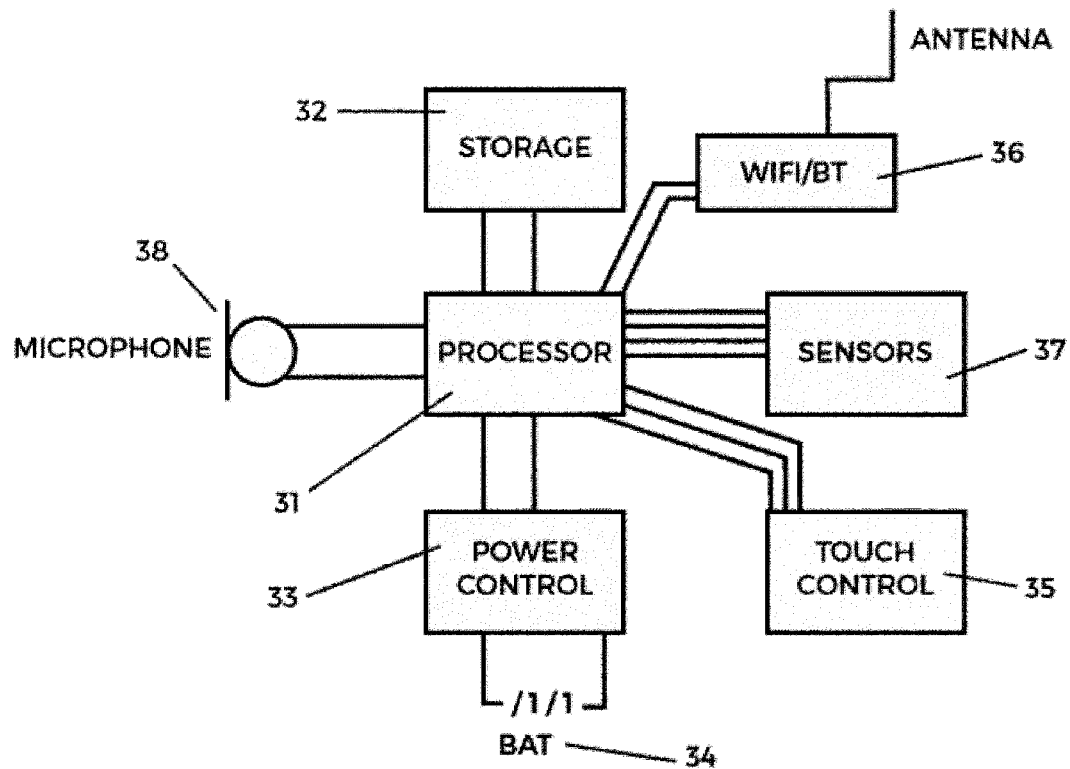
FIG. 12 Shows a block circuit diagram of a circuit for use with a wearable device.

Referring now to FIG. 12 circuit 24 is shown in block diagram form. It will be appreciated that this circuit may also be utilized in the previous embodiments. It will also be appreciated that some or all of the components may be incorporated in a wearable device depending upon the functionality required.

Circuit 24 includes a microprocessor 31 having associated storage 32, typically flash RAM, and a power supply 33 supplying power from a battery 34. Microprocessor 31 may include a media player to play music stored in storage 32 or supplied as a stream from communications circuit 36. Battery 34 may be recharged via a cable or wirelessly. User inputs 35, such as touch sensors, allow user control of volume, mode, content etc. A communications circuit communicates with earpiece 23 to supply a signal to drive a speaker via circuit 27 as well as to communicate with external devices. Such external communications may include Wi-Fi, Bluetooth, cellular or other wireless communications to upload or stream content.

A range of sensors 37 may be connected to microprocessor 31 such as biometric or other sensors including a heart rate monitor, temperature sensor, movement sensor, accelerometer, location sensor, GPS, gyroscope, altimeter etc.

A microphone 38 may also be provided for user control via a voice recognition system or to monitor environmental sound. The microphone may also be employed in a noise cancellation system.

As well as providing a record of user activity the biometric and other sensors may be used to intelligently control operation of the wearable device. The output volume of a signal supplied to the earpiece may be adjusted based on the output of one or more biometric sensor (e.g. louder during intense activity or loud background noise). A play list stored in storage 32 may be selected based on the intensity of user activity. A water sensor may be provided which pauses music when the water detector detects the presence of water.

The wearable device may also communicate location and/or biometric data to a cloud based system that analyses biometric and location data and provides coaching tips, directions and other derived information to a user.

A sensor may also detect when the positioning magnets are properly aligned and generate a sound to indicate good alignment.

There is thus provided a wearable device with the following advantages:
a. Increased stability of the device on the ear during energetic and varied movements.
b. Centring the mass of the device on the ear in a way that increases the strength of the anchoring.
c. Appropriate centre of mass and weight distribution for attachment during energetic and varied movements.
d. Correct balance of pull force and cushioning to ensure secure hold over long periods of time, without causing discomfort.
e. Standardisation of sizing allows for fit on wide range of ear shapes for mass market.
f. Magnetic system is easy to integrate into existing manufacturing processes.
g. Improved positioning of earbud to rest in good position for audio consumption.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

The invention claimed is:

1. A wearable device for attachment to an ear of a user comprising:
an earpiece including a speaker and a first magnetic element; and
a body section including a hook for attachment about an ear of a user and configured to engage around an upper part of a region connecting the ear to a skull of the user, the body section further including a media player housed within the body section and a second magnetic element,
wherein the earpiece is movable relative to the body section and the earpiece and body section are configured so that when the body section is hooked about the ear the first magnetic element and second magnetic element are adapted to be magnetically attracted to each other through the ear to retain the device in place.

2. A wearable device as claimed in claim 1 wherein the second magnetic element is positioned so as to be proximate a concha of the ear when the body section is worn on the ear of the user.

3. A wearable device as claimed in claim 1 wherein the hook is twisted so as to direct a weight of the body section into the user's skull.

4. A wearable device as claimed in claim 1 wherein the hook is flexible to wrap around the ear of the user.

5. A wearable device as claimed in claim 1 wherein the earpiece is connected to the body section via a flexible section.

6. A wearable device as claimed in claim 5 wherein when the first and second magnetic elements are proximate each other the flexible section is drawn around the ear of the user in use.

7. A wearable device as claimed in claim 1 wherein the first magnetic element is located at a distal end of the earpiece.

8. A wearable device as claimed in claim 5 wherein the earpiece includes a face at a distal end that is inclined at an angle of between plane 30° and 60° with respect to a face of the earpiece that engages the user's ear in use.

9. A wearable device as claimed in claim 1 wherein the earpiece is separate from the body section.

10. A wearable device as claimed in claim 7 wherein the earpiece communicates with the body section via a wireless connection.

11. A wearable device as claimed in claim 1 wherein the body section includes multiple magnets spaced at intervals to enable attachment of the earpiece at a plurality of positions to suit a range of ear shapes.

12. A wearable device as claimed in claim 1 wherein the body section includes an extendable section to adjust a relative position of the second magnetic element with respect to the body section to allow adjustment of the relative position of the second magnetic element to accommodate different ear shapes.

13. A wearable device as claimed in claim 1 wherein the earpiece includes an extendable section attached to the first magnetic element allowing positioning of the first magnetic element towards or away from the earpiece to allow adjustment to accommodate different ear shapes.

14. A wearable device as claimed in claim 1 including a microprocessor housed in the body section.

15. A wearable device as claimed in claim 1 including one or more biometric sensors selected from a heart rate monitor, temperature sensor, movement sensor, microphone, accelerometer, location sensor, GPS, gyroscope, altimeter and acoustic sensor.

16. A wearable device as claimed in claim 11 including a wireless communication circuit for uploading or streaming content from another device.

17. A wearable device as claimed in claim 16 wherein the wireless communication circuit is capable of communicating with a cellular communication system.

18. A wearable device as claimed in claim 1 wherein the device is adapted to communicate location and/or biometric data to a cloud based system that analyses biometric and location data and provides coaching tips, directions and other derived information to the user.

19. A wearable device as claimed in claim 1 wherein a coating is applied to portions of the body section formed of a thermoplastic elastomer or silicone material.

\* \* \* \* \*